United States Patent
Hahn et al.

(10) Patent No.: US 10,916,043 B2
(45) Date of Patent: Feb. 9, 2021

(54) APPARATUS, METHOD AND COMPUTER PROGRAM FOR GENERATING A TEMPLATE FOR ARRANGING AT LEAST ONE OBJECT AT AT LEAST ONE PLACE

(75) Inventors: Horst Hahn, Bremen (DE); Uwe Siems, Bremen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 1033 days.

(21) Appl. No.: 11/945,106

(22) Filed: Nov. 26, 2007

(65) Prior Publication Data
US 2009/0138788 A1  May 28, 2009

(51) Int. Cl.
```
G16H 30/20      (2018.01)
G16H 30/40      (2018.01)
G06T 11/60      (2006.01)
```
(52) U.S. Cl.
CPC ............ *G06T 11/60* (2013.01); *G16H 30/20* (2018.01); *G16H 30/40* (2018.01)

(58) Field of Classification Search
CPC .... G06F 17/211; G06F 17/212; G06F 17/248; G06K 9/00483; G06T 11/60; G16H 30/20; G16H 30/40
USPC ........ 715/200, 222, 243, 246; 382/195, 131, 382/132, 190, 209, 214
See application file for complete search history.

(56) References Cited

U.S. PATENT DOCUMENTS

| | | | |
|---|---|---|---|
| 4,127,774 A * | 11/1978 | Gillen | 378/165 |
| 5,452,416 A | 9/1995 | Hilton et al. | |
| 6,354,737 B1 * | 3/2002 | Hufe et al. | 378/205 |
| 6,411,731 B1 * | 6/2002 | Saito | 382/173 |
| 6,631,204 B1 * | 10/2003 | Smith | G06K 9/52 128/922 |
| 6,771,801 B1 * | 8/2004 | Fisher | H04N 1/00164 283/67 |
| 2002/0154820 A1 * | 10/2002 | Kaneko et al. | 382/209 |
| 2004/0028290 A1 * | 2/2004 | Gamble | G06T 11/60 382/284 |
| 2004/0183830 A1 * | 9/2004 | Cody et al. | 345/752 |
| 2004/0268299 A1 * | 12/2004 | Lei | G06F 9/451 717/106 |
| 2005/0078857 A1 * | 4/2005 | Park | 382/128 |

(Continued)

FOREIGN PATENT DOCUMENTS

DE   10125504 A1   2/2008

OTHER PUBLICATIONS

Digital Imaging and Communications in Medicine (DICOM), Supplement 60: Hanging Protocols, pp. 108, published Jan. 18, 2005 (Year: 2005).*

*Primary Examiner* — Stephen S Hong
*Assistant Examiner* — Ahamed I Nazar
(74) *Attorney, Agent, or Firm* — Ellen M. Bierman; Lowe Graham Jones PLLC

(57) ABSTRACT

Methods and apparatus for generating a template for arranging at least one object at least one place, wherein the at least one object is characterized by at least one feature, wherein the methods and apparatus facilitate: providing at least one initial object, arranging the at least one initial object at the at least one place, and generating the template by assigning to the at least one place the at least one feature of the at least one initial object, which has been arranged at the at least one place.

18 Claims, 6 Drawing Sheets

(56) References Cited

U.S. PATENT DOCUMENTS

| | | | |
|---|---|---|---|
| 2005/0084154 A1* | 4/2005 | Li | G06K 9/4652 |
| | | | 382/190 |
| 2005/0134939 A1* | 6/2005 | Ikeda et al. | 358/471 |
| 2005/0143641 A1* | 6/2005 | Tashiro | 600/407 |
| 2006/0093198 A1* | 5/2006 | Fram | G06T 7/0012 |
| | | | 382/128 |
| 2006/0106642 A1* | 5/2006 | Reicher | G06T 7/38 |
| | | | 705/2 |
| 2006/0221779 A1* | 10/2006 | Matsushita | G06F 17/3028 |
| | | | 369/30.01 |
| 2006/0233430 A1* | 10/2006 | Kimura | G06T 7/30 |
| | | | 382/128 |
| 2006/0238546 A1* | 10/2006 | Handley | H04N 1/0045 |
| | | | 345/619 |
| 2006/0239573 A1* | 10/2006 | Novatzky | G16H 30/20 |
| | | | 382/239 |
| 2006/0259855 A1* | 11/2006 | Crucs | 715/517 |
| 2006/0279555 A1* | 12/2006 | Ono | 345/173 |
| 2007/0019853 A1* | 1/2007 | Luo | 382/132 |
| 2007/0030520 A1* | 2/2007 | Sugimoto | 358/1.18 |
| 2007/0036411 A1* | 2/2007 | Guetat et al. | 382/128 |
| 2007/0159962 A1* | 7/2007 | Mathavu | H04N 1/00408 |
| | | | 370/219 |
| 2007/0230758 A1* | 10/2007 | Fan et al. | 382/128 |
| 2007/0248254 A1* | 10/2007 | Mysore Siddu et al. | 382/131 |
| 2008/0028298 A1* | 1/2008 | Kaneko | 715/243 |
| 2008/0089590 A1* | 4/2008 | Isomura | G06F 17/3028 |
| | | | 382/217 |
| 2008/0118139 A1* | 5/2008 | Huo et al. | 382/132 |
| 2008/0120576 A1* | 5/2008 | Kariathungal et al. | 715/863 |
| 2008/0199199 A1* | 8/2008 | Kato et al. | 399/81 |
| 2008/0267471 A1* | 10/2008 | Yu et al. | 382/128 |
| 2009/0129644 A1* | 5/2009 | Daw et al. | 382/128 |

* cited by examiner

| 15 | 20 | 21 | 22 | 23 |
|---|---|---|---|---|
| a1 | a2 | a3 | a4 | w1 |
| b1 | b2 | b3 | b4 | w2 |
| c1 | c2 | c3 | c4 | w3 |
| d1 | d2 | d | d4 | w4 |
| e1 | e2 | e3 | e4 | w5 |
| f1 | f2 | f3 | f4 | w6 |
| g1 | g2 | g3 | g4 | w7 |
| h1 | h2 | h3 | h4 | w8 |
| i1 | i2 | i3 | i4 | w9 |
| j1 | j2 | j3 | j4 | w10 |
| k1 | k2 | k3 | k4 | w11 |

APPARATUS, METHOD AND COMPUTER PROGRAM FOR GENERATING A TEMPLATE FOR ARRANGING AT LEAST ONE OBJECT AT AT LEAST ONE PLACE

FIELD OF THE INVENTION

The invention relates to an apparatus, a method and a computer program for generating a template for arranging at least one object at least one place. The invention relates further to an apparatus, a method and a computer program for arranging at least one object at least one place using the template.

BACKGROUND OF THE INVENTION

In medical imaging in general and in soft-copy image reading in particular, there is a clear trend towards imaging protocols that comprise multiple image series. In the following, image series can refer to a series of contiguous images or to a single image, respectively. These image series are acquired either to cover multiple body regions, to provide different contrasts or image characteristics of the same body region, or to follow-up a given body region over time, or a combination thereof. In all of these cases, in particular if the number of different image series for a given reading task is large, for example ten or more, the question arises how to arrange these images on one or several monitors. In modern computer systems, in analogy to the film-based scenario, this question is answered by templates, which define the position of a given image series on the screen or screens and the combination of multiple image series. In existing computer systems, the available templates are rather fixed or steered by a rule-based approach that can be configured by a trained technician. However, with growing complexity of multi-series imaging acquisition protocols or with a growing need for individualized templates that reflect the requirements of specific examinations or of individual users, or with a combination thereof, both systems, the fixed set of templates and the rule-based approach, become increasingly inefficient.

SUMMARY OF THE INVENTION

It is an object of the present invention to provide an apparatus, a method and a computer program for generating a template for arranging at least one object at least one place, wherein the efficiency is improved, in particular, wherein a definition, which object has to be placed at which place, is simplified. It is a further object of the present invention to provide an apparatus, a method and a computer program for arranging at least one object at least one place using the template.

In an aspect of the present invention an apparatus for generating a template for arranging at least one object at least one place is provided, wherein the at least one object is characterized by at least one feature, wherein the apparatus comprises: a providing unit for providing at least one initial object, an initially arranging unit for arranging the at least one initial object at the at least one place, and an assigning unit for generating the template by assigning to the at least one place the at least one feature of the at least one initial object, which has been arranged at the least one place.

A template can easily generated by arranging the at least one initial object at the at least one place. This is preferentially done by a user, for example, a radiologist. After this arranging of the at least one initial object at the at least one place, the template can be generated by simply assigning to the at least one place the at least one feature of the at least one initial object, which has been arranged at this at least one place. Thus, a template can be generated by arranging one or several initial objects at one or several places. This simplifies and increases the efficiency of a generation of a template.

Preferentially, multiple initial objects are present, wherein each initial object comprises multiple features. Furthermore, preferentially multiple places are present, at which the multiple of initial objects can be arranged.

The initial object is preferentially an image, in particular a two-dimensional image or a series of two-dimensional images, which can be any series of two-dimensional images, which might be a three-dimensional image. The image is preferentially a medical image, which has been generated by a medical imaging device like a computed tomography device, a magnetic resonance imaging device, an ultrasound imaging device, an x-ray projection imaging device or a nuclear imaging device like a positron emission imaging device or a single photon emission computed tomography device. A series of contiguous images, in particular, a series of contiguous two-dimensional images, in particular, slices, can also be regarded as three-dimensional image. These image series can be acquired either to cover multiple body regions, to provide different contrasts or image characteristics of the same body region, or to follow-up a given body region over time, or a combination thereof.

The at least one place, in particular, the multiple places, is at least one place on a screen of a monitor. If multiple places are present, these places are preferentially distributed on a screen of monitor or on two or more screens of two or more monitors. Thus, preferentially medical images are arranged at places distributed over one or several screens of one or several monitors. The distribution of the places on at least one screen is preferentially denoted as screen layout or viewer grid, which is, for example, a 2×2 or a 3×3 screen layout, wherein 2×2 or 3×3 places are provided on at least one screen for simultaneously displaying four or nine objects, in particular four or nine image series, on one or several screens, respectively.

The features, which characterize the at least one initial object and/or the at least one object, are, for example, features provided in the DICOM standard. These features, are, for example, numerical or alpha-numerical data, which denote, for example, the imaging device or modality, which has to be used for generating an image, the element, for example, the part of a patient, which is shown by the image, the number of slices in the image, the thickness of a slice within the image, the resolution of an image, the employed imaging technique or sequence, any applied contrast agent or drug, the orientation of the image, etc.

The at least one initial object can be an arbitrary object, which can, for example, be chosen by a user like a radiologist. For example, a user can choose different images showing the same element, for example, the same part of a patient, wherein for generating the different images different imaging parameters have been used, for example, the images are generated in different orientations or by different measuring sequences or by different modalities. The different objects chosen by the user are regarded as initial objects and these initial objects are arranged at the different places. For example, different images are arranged at different places on at least one screen of at least one monitor.

The initially arranging unit is preferentially adapted such that a user like a radiologist can choose an initial object and arrange the chosen initial object at a desired place. The initially arranging unit comprises preferentially a graphical user interface of a computer system, which is adapted for selecting an object as an initial object and arranging this initial object at a desired place on a screen of a monitor. In particular, the graphical user interface allows a user to select and arrange an object by a drag-and-drop operation, wherein preferentially a mouse or a keyboard is used.

The initially arranging unit can also be adapted such that objects, which can be regarded as initial objects, are arranged in accordance with an existing template, in particular loaded from a storage unit, wherein the arranged objects can be modified or not and wherein a new template is generated by assigning features of the arranged und possibly modified objects to the places, at which they are arranged, by the assigning unit.

It is preferred that the assigning unit is adapted for assigning multiple features to the at least one place and for assigning weights to the multiple features of the at least one place. Preferentially, to each feature, which has been assigned to a place, a weight, in particular a weighting value, is assigned. This allows considering the features differently by the weights, if they are used for determining a similarity between an actual object and a place, which will be described in more detail further below.

Preferentially, at least some or all objects are characterized by several features, wherein preferentially only some of the features are assigned to a place.

It is further preferred that the apparatus for generating a template further comprises a modifying unit for modifying the template by modifying an arrangement of an initial object of the at least one initial object at a place of the at least one place. The template can simply be modified by modifying an arrangement of an initial object of the at least one initial object at a place of the at least one place, wherein the assigning unit modifies the template by assigning to the at least one place, at which another or a modified initial object has been placed, the at least one feature of this initial object. For example, if images as initial objects have been chosen by a user and arranged on different places on a screen of a monitor for generating a template, this template can be modified by exchanging at least one of the images, which have been arranged on the places, by another image, wherein at least some predefined or all of the characterizing features of the other image are assigned to the place, at which this other image is arranged now, for modifying the template. Moreover, a template can be modified by simply adding an object to an empty place or by removing an object from an occupied place or by changing the screen layout or viewer grid, respectively.

It is further preferred that a new template is created by arranging objects in accordance with a template and by generating a new template using the newly assigned objects as initial objects, i.e. features of the newly assigned objects are assigned to the respective places. It is further preferred that the new arrangement of objects is modified, wherein the newly added and modified objects are used for generating a new template by assigned features of the objects to the respective places.

One or several templates are preferentially stored in a storing unit like a memory of a computer system and can be loaded for arranging at least one object at least one place.

In a further aspect of the present invention an apparatus for arranging at least one object at least one place using a template is provided, wherein the at least one object is characterized by at least one feature, wherein the apparatus is provided with a template generated by an apparatus for generating a template for arranging at least one object at at least one place, wherein the apparatus for generating a template comprises: a providing unit for providing at least one initial object, an initially arranging unit for arranging the at least one initial object at the at least one place, and an assigning unit for generating the template by assigning to the at least one place the at least one feature of the at least one initial object, which has been arranged at the least one place, wherein the apparatus for arranging at least one object at least one place using a template comprises: a similarity unit for determining a degree of similarity of an object of the at least one object to a place of the at least one place with respect to the at least one feature of the object and the at least one feature assigned to the place in the template, and an arranging unit for arranging the at least one object at the at least one place depending on the determined degree of similarity.

Since the at least one object is arranged at the at least one place depending on the determined similarity of an object to a place, wherein the at least one feature assigned to this place and the at least one feature characterizing the object are used, the at least one object can easily and efficiently be arranged at the at least one place in accordance with the template.

The features, which are used for determining a degree of similarity and for generating the template, can be predefined. In particular, they are preferentially a subgroup of all characterizing features of the objects. The subgroup can be defined by assigning to all features, which are not an element of the subgroup, a zero weight.

Preferentially, several objects, in particular, several images, have to be arranged at different places, in particular, on at least one screen of at least one monitor of a computer system.

It is further preferred that multiple objects and multiple places are present, wherein the similarity unit is adapted for determining the degree of similarity for each combination of objects and places and wherein the arranging unit is adapted for arranging the objects at the places in accordance with the determined degrees of similarity of the combinations. Preferentially, firstly an object is arranged on a place, which belongs to the combination with the largest degree of similarity, then an object is arranged at a place, which belongs to the combination comprising the second largest degree of similarity among the remaining objects and places, and so on. This increases the quality of the arrangement of the objects in accordance with the template.

For example, the similarity of an object to the features of a given template place can be computed by the sum of the similarity of all employed features. Similarity is commonly a value between 0 and 1, whereas 1 corresponds to perfect similarity and 0 corresponds to the least possible similarity or simply to the opposite of perfect similarity in a binary fashion. Such similarity measure can also be computed for alphanumeric features, for example by character-wise string comparison and subsequent normalization by the length of the feature or template feature, respectively. For any feature, in particular numerical and alphanumerical, the similarity measure could be implemented in a fuzzy fashion such that any value between 0 and 1 is possible and corresponds to more or less pronounced similarity. Also a tolerance could be specified resulting in a high similarity value even if the feature differs from the template feature by a value less than the tolerance value. Instead of the simple sum, also the weighted sum can be used. For template features, which should be mandatorily matched for an object assignment, a value of infinity can be used for the weight. This infinite value can be encoded by a special number, for example −1.

Then, as soon as a feature is not matched, whose weight is −1, the similarity of the object with respect to the features of a given template place would be zero. For all other cases, it is possible to compute the similarity in a normalized fashion by dividing by the sum of all feature weights. Also, instead of a summarized similarity measure, a multiplicative similarity measure could be implemented or any other combination of single feature similarity measures.

It is further preferred that the arranging unit is adapted for arranging an object of the at least one object at a place of the at least one place only if the determined similarity exceeds a certain value. This value could be a predetermined threshold or also an adaptive threshold, which for example is computed by the statistics over several or all similarity values. This ensures that an object is arranged at a place only if at least a certain degree of similarity is present between the object and the place with respect to the features assigned to the place in the template and the characterizing features of the object.

Preferentially, an object of the at least one object, which is not arranged on a place of the at least one place, is assigned to a remaining list. The at least one object assigned to the remaining list can be shown to a user, for example, via a screen of a monitor of a computer system. In particular, a user can select, for example, by using a graphical user interface, preferentially providing a drag-and-drop operation, an object, in particular, an image, of the remaining list and arrange this object on a place, in particular, on at least one screen of at least one monitor, wherein at least some features of this object are assigned to this place for modifying a template, which has preferentially been loaded from a storing unit, in which preferentially one or more templates are stored. Also, all remaining objects or images could be automatically arranged on the screen. The automatic arrangement of remaining objects images could, in a preferred embodiment of the invention, automatically be presented to the user after the last regularly arranged object or image, respectively. The automatic arrangement of remaining objects could, for example, be ordered in the order of object creation or image acquisition, respectively, or in the order of maximum similarity values for each object.

For every place of the template, also one or several further parameters can be stored with the template. These parameters could relate to specific details of the object presentation. In case of medical images, these parameters could relate to the contrast and brightness of the visualization, to the current magnification, orientation, or slice number, or to the visualization mode, for example slice rendering, volume rendering, projection rendering, etc. When new objects are arranged by using a template, all of these parameters can then be applied to the newly arranged objects or images or to their places or viewers, respectively.

It is further preferred that multiple objects are present, wherein the arranging unit is adapted for arranging objects, for which a similar degree of similarity is determined, in dependence on features of these objects, which have not been assigned by the initially assigning unit of the apparatus for generating a template. Two or more objects have a similar similarity, if the degree of similarity is identical or if an absolute distance between the degrees of similarity of these objects is below a predetermined threshold value. Features, which characterize these objects and which are not part of the template, are features, which preferentially do not belong to a kind or class of feature like, for example, the time of generating an image or the kind of element or the location of an element shown on an image, which has been assigned to a place by the assigning unit for generating a template. The location of an element is preferentially a location of a part of a patient, which is shown in the respective image, with respect to the patient.

This allows arranging objects on places, even if they show a similar degree of similarity with respect to the features of the template.

The apparatus for arranging at least one object at least one place using the template, preferentially further comprises a plausibility determination unit for determining the plausibility of a feature of the at least one object, wherein the similarity unit and/or the arranging unit are adapted for ignoring or considering with a reduced weight a feature, the plausibility of which is below a predefined threshold. This increases the quality of the arrangement of objects at places in accordance with the template. Also, instead of reducing the weight for a feature in case of low plausibility, the feature could be automatically corrected, if available, to a more suitable value before entering the similarity computation.

For example, in a situation where more than one feature are indicative for the position of an object, in particular for the anatomical position of a radiological image or for the imaged body part or organ, one feature could be of a lesser reliability than the other feature or features and thus be treated as implausible. One feature encoding the anatomical position, in case of a tomographic radiological image, could be provided by the coordinate system delivered with the image, while a second such feature could be a string encoding the imaged body part. For example, the coordinate system, which cannot be influenced by the operating personnel, could be estimated to be more reliable than the descriptive alphanumeric string, that is edited by the operating personnel. If the imaged body part is one of the available features, the corresponding value could be corrected if, for example, one "foot" image is found within 2 cm distance of a large number of "head" images, whereas all other "foot" images are more than 100 cm distant from the closest "head" image.

It is further preferred that the apparatus for generating a template is adapted for providing multiple templates, wherein the apparatus as defined in claim 4 further comprises a selecting unit for selecting a template of the multiple of templates by determining for each template a degree of similarity, which depends on the degrees of similarity of the objects to the places with respect to the at least one feature of the respective template, and by selecting a template of the multiple templates having a similarity above a threshold and/or having a the maximum degree of similarity. Preferentially, multiple templates generated by the apparatus for generating a template are stored in a storing unit and for each of the templates and for each combination of object and place of the respective template a degree of similarity is determined, wherein the determined degrees of similarity of the combinations of a template are preferentially summed up for determining a degree of similarity for the respective template. Also, the determined degrees of similarity of the combinations of a template could be combined in a multiplicative fashion. It is further preferred that for each template all or a predefined number of the objects are virtually arranged at the places in accordance with the respective template, wherein the degree of similarity of the combinations of the respective template is summed up or multiplied to determine a degree of similarity of the respective template. Furthermore, only the objects, which belong to combinations having a degree of similarity larger as a predefined threshold, can be used for determining the degree of similarity of the respective template. This allows selecting a template of a multiple of templates, which is suited best for the objects, which have to be arranged, by selecting a template having the highest degree of similarity.

It is further preferred that the generation of templates and the arranging of object in accordance with a template is performed by a single system, in particular, a single computer system, in particular, comprising the apparatus for generating a template and the apparatus for arranging objects using a template.

In a further aspect of the present invention a method for generating a template for arranging at least one object at least one place is provided, wherein the method comprises following steps: providing at least one initial object, arranging the at least one initial object at the at least one place, and generating the template by assigning to the at least one place the at least one feature of the at least one initial object, which has been arranged at the least one place.

In a further aspect of the present invention a method for arranging at least one object at least one place using the template is provided, wherein the method comprises following steps: providing at least one initial object, arranging the at least one initial object at the at least one place, and generating the template by assigning to the at least one place the at least one feature of the at least one initial object, which has been arranged at the least one place, wherein the method for arranging at least one object at least one place using a template comprises following steps: determining a degree of similarity of an object of the at least one object to a place of the at least one place with respect to the at least one feature of the object and the at least one feature assigned to the place in the template, arranging the at least one object at the at least one place depending on the determined degree of similarity.

In a further aspect of the present invention a computer program for generating a template for arranging at least one object at least one place is provided, wherein the computer program comprises program code means for causing a computer to carry out the steps of the method as defined in claim 11, when the computer program is run on a computer controlling an apparatus as defined in claim 1.

In a further aspect of the present invention a computer program for arranging at least one object at least one place using a template is provided, wherein the computer program comprises program code means for causing a computer to carry out the steps of the method as defined in claim 12, when the computer program is run on a computer controlling an apparatus as defined in claim 4.

It shall be understood that the apparatus of claim 1, the apparatus of claim 4, the method of claim 11, the method of claim 12, the computer program of claim 13 and the computer program of claim 14 have similar and/or identical preferred embodiments, in particular as defined in the dependent claims.

It shall be understood that preferred embodiments of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following FIG. 3 shows schematically and exemplarily a data structure defining a template.

DETAILED DESCRIPTION OF PREFERRED EMBODIMENTS

Figure 1:
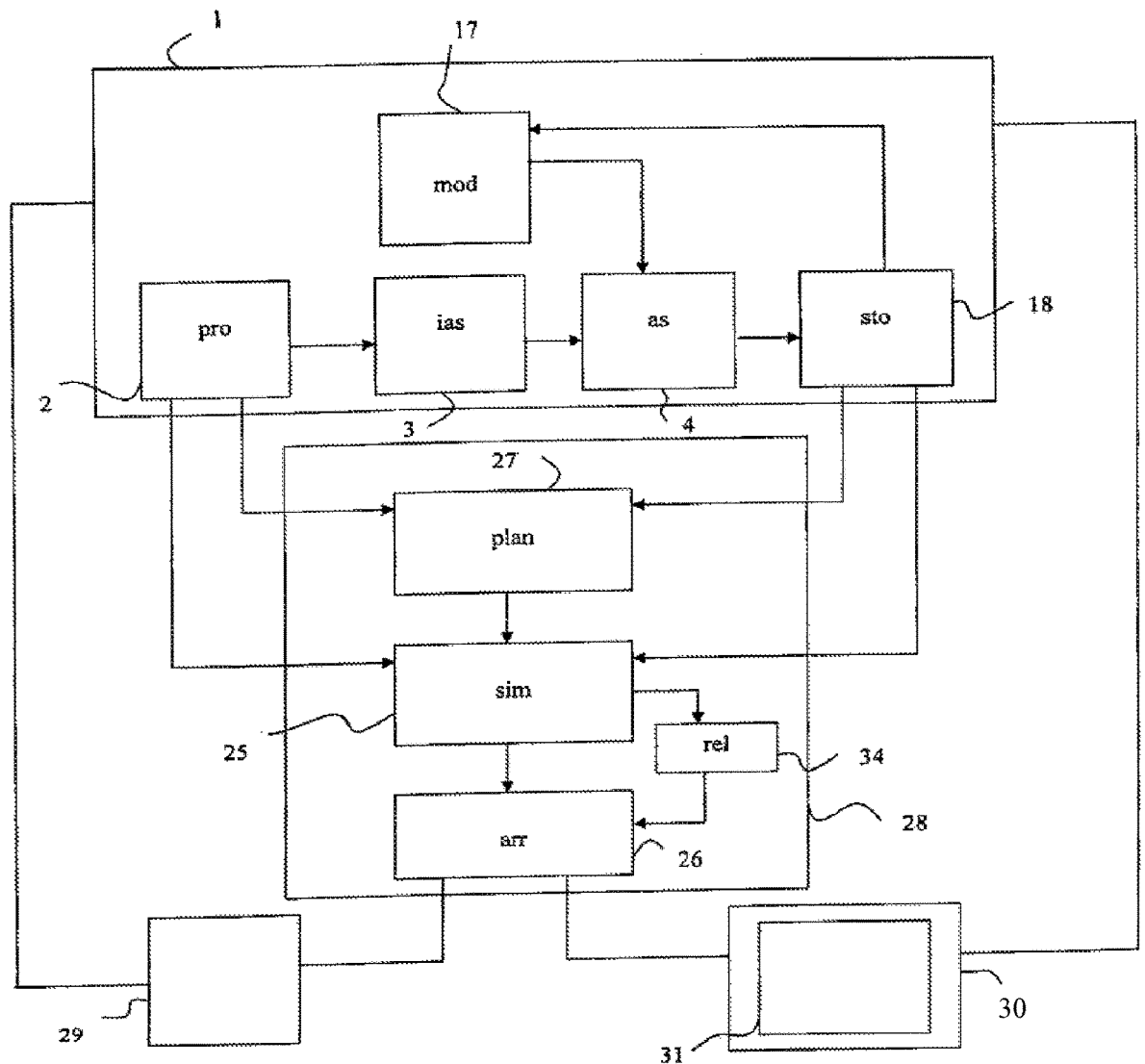
FIG. 1 shows schematically and exemplarily an apparatus for generating a template for arranging at least one object at at least one place and an apparatus for arranging at least one object at least one place using the template.

FIG. 1 shows exemplarily and schematically an apparatus 1 for generating a template for arranging at least one object at at least one place, in the following referred to as generating apparatus 1, and an apparatus 28 for arranging at least one object at least one place using a template, in the following referred to as arranging apparatus 28.

The objects are characterized by at least one feature.

The generating apparatus 1 comprises a providing unit 2 for providing at least one initial object, an initially arranging unit 3 for arranging the at least one initial object at the at least one place and an assigning unit 4 for generating the template by assigning to the at least one place the at least one feature of the at least one initial object, which has been arranged at the at least one place.

The initial object is preferentially characterized by several features, wherein preferentially not all of these features are assigned to the at least one place, in particular, preferentially only a predefined subgroup of features is assigned to the at least one place, i.e. preferentially kinds or classes of features are predefined, wherein features, which belong to these kinds or classes, like an imaging modality used for generating an image, slice thickness of an image, imaging parameters etc., are assigned to the at least one place.

The initial object is, preferentially, a medical image, wherein preferentially several initial objects, i.e. in this embodiment several medical images of the same object are present. The medical images belong preferentially to the same case, i.e., in particular, they show the same patient and preferentially the same examination. The providing unit 2 is, in this embodiment, a storage unit, in which different medical images are stored. In another embodiment, the providing unit is for example a medical imaging device, which generates medical images.

The initially arranging unit 3 is, in this embodiment, an arranging unit, which allows a user, in particular, a radiologist, to arrange at least one initial object, in this embodiment, several initial objects, at least one place, in this embodiment, different places. The initially arranging unit 3 preferentially comprises a graphical user interface, which allows a user via, in this embodiment, a drag-and-drop operation to arrange the several objects at the several places by using an input unit 29. The input unit 29 comprises preferentially a keyboard and/or a mouse.

Figure 2:
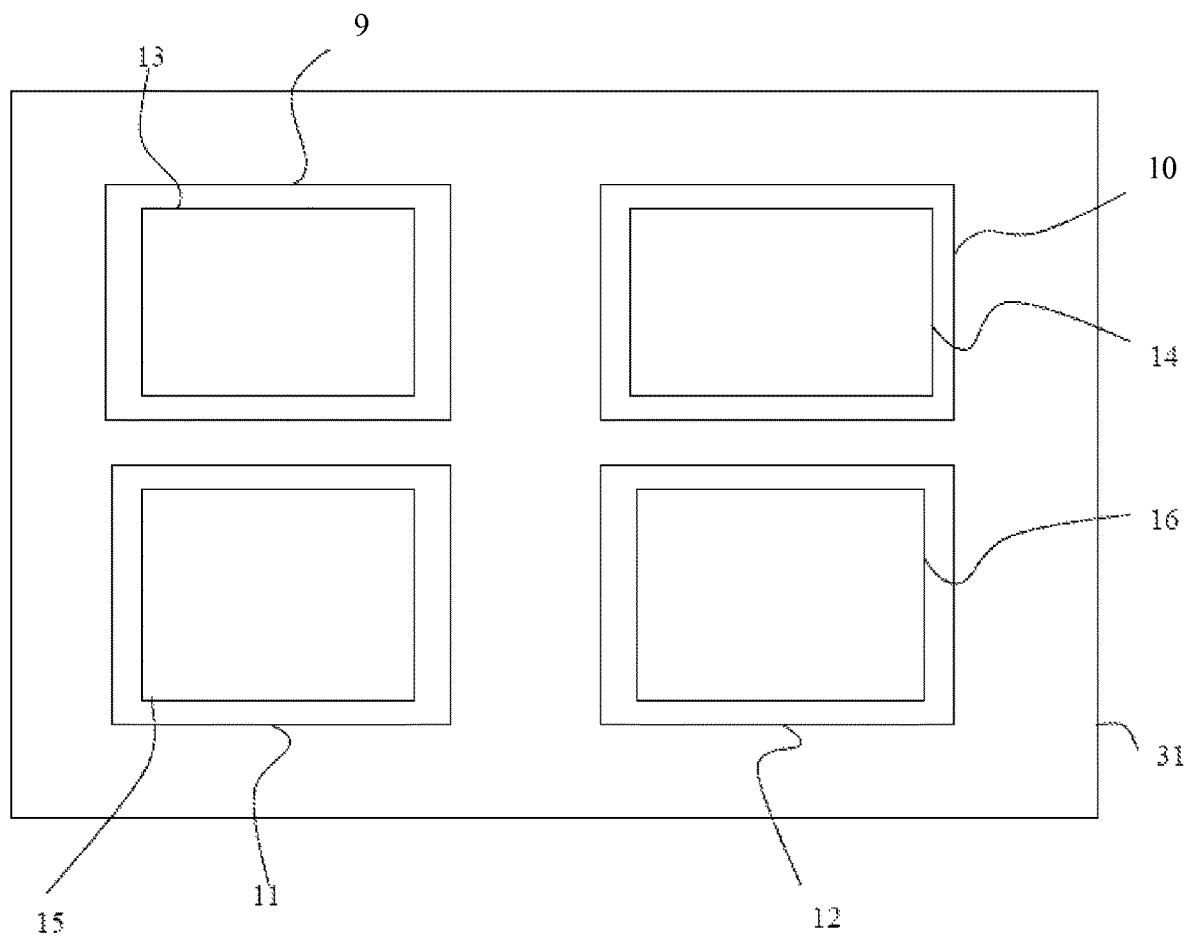
FIG. 2 shows schematically and exemplarily a screen on which several places are distributed, wherein at each place an initial object is arranged, for generating a template.

An arrangement of initial objects 13, 14, 15, 16 at places 9, 10, 11, 12 on a screen 31 of a monitor 30, which has been generated by using the initially arranging unit 3, is schematically and exemplarily shown in FIG. 2.

FIG. 2 shows four objects 13, 14, 15, 16 arranged at four places 9, 10, 11, 12 distributed on the screen 31. In other embodiments, another number of objects can be arranged at another number of places on one or more screens of one or more monitors. Each place 9, 10, 11, 12 preferentially comprises a viewing element for viewing an object 13, 14, 15, 16.

Each of the initial objects 13, 14, 15, 16 comprises at least one feature, in this embodiment, several features, which characterize the respective object and which will be used for generating a template.

The assigning unit 4 generates a template by assigning, in this embodiment, the features of the object 13 to the place 9, the features of the object 14 to the place 10, the features of the object 15 to the place 11 and the features of the object 16 to the place 12. The features of an object, which are assigned to a place, can be predefined or, for example, defined by a user, i.e. not all characterizing features of an object have to be assigned to a place. Preferentially, a subgroup of features can be defined, which are assigned to a place.

By assigning features of the objects to the respective places, a template is generated. A data structure of template is schematically and exemplarily shown in FIG. 3.

FIG. 3 shows a template 33 for the four places 9, 10, 11, 12. The features a1 . . . k1 of object 13 have been assigned to the place 9 and are stored in column 19. The features a2 . . . k2 of the object 14 have been assigned to the place 10 and are stored in column 20. The features a3 . . . k3 of the object 15 have been assigned to the place 11 and are stored in column 21. The features a4 . . . k4 of the object 16 have been assigned to the place 12 and are stored in the column 22.

Referring again to FIG. 1, the generating apparatus 1 further comprises a modifying unit 17 for modifying the template 33 by modifying an arrangement of an initial object of the at least one initial object at a place of the at least one place. In this embodiment, for modifying the template 33, which is stored in the storage unit 18, after the template has been generated by the assigning unit 4, the template 33 is loaded into the modifying unit 17 from the storage unit 18. The template 33 comprises, in this embodiment, features indicating the object, i.e., in this embodiment, the image, which was arranged at the respective place for generating the template. The modifying unit 17 shows the objects indicated by the features in the template 33 at the respective places on the screen 31 of the monitor 30. A user can now substitute at least one of the initial objects 13, 14, 15, 16 at the places 9, 10, 11, 12 by another object, for example, by another medical image for modifying the arrangement of the initial objects on the places by using the input unit 29 and a graphical user interface, which preferentially provides a drag-and-drop operation. The modified arrangement of initial objects on the places is transferred to the assigning unit 4, which assigns features of the newly added objects to the respective places for generating a modified template.

The assigning unit 4 is preferentially adapted for assigning weights $w_1 \ldots w_{11}$ to the features stored in the template. The assignment of the weights $w_1 \ldots w_{11}$ to the features can be predefined or defined or modified by a user using the input unit 29. In FIG. 3, the weights are stored in column 23.

The arranging apparatus 28 uses the template 33 generated by the generating apparatus 1. The arranging apparatus 28 comprises a similarity unit 25 for determining a degree of similarity of an object of the at least one object to a place of the at least one place with respect to the at least one feature of the object and the at least one feature assigned to the place in the template. In this embodiment, the similarity unit 25 receives several medical images 5, 6, 7, 8, in this embodiment, from the providing unit 2 and the template 33 from the storage unit 18. In another embodiment, the medical images can be provided from another unit, for example, another storage unit or directly from another medical imaging device. The similarity unit 25 determines for each combination of the objects 5, 6, 7, 8 and the places 9, 10, 11, 12 a degree of similarity with respect to the features of the object and the features assigned to the respective place in the template. Thus, for each combination a degree of similarity is determined by comparing the features of the respective object with the features assigned to the respective place in the template 33.

The arranging apparatus 28 further comprises an arranging unit 26 for arranging the at least one object at the at least one place depending on the determined degree of similarity. In this embodiment, the arranging unit 26 arranges a first object at a first place according to the combination having the largest degree of similarity. Then, the arranging unit 26 arranges a second object at a second place according to the combination having the second largest degree of similarity, without considering combinations comprising the first object or the first place, and so forth. The arranging unit 26 is further preferentially adapted such that an object is not arranged at a place, if the degree of similarity determined for this combination of object and place is below a predetermined threshold. Moreover, the arranging unit 26 is preferentially adapted such that an object, which is not arranged on a place by using the template, for example, because the degree of similarity between this object and each of the places is below the threshold or because there are more objects provided than places, is assigned to a remaining list, which comprises objects, which have not been arranged on a place, in this embodiment, on the screen 31 of the monitor 30. The objects of the remaining list can, in particular, initiated by a user using the input unit 29, be shown on the screen 31 of the monitor 30. An object of the remaining list can then, for example, be used for a substitution of an initial object of the template 33 using the input unit 29, in particular, using a graphical user interface comprising drag-and-drop functionality.

The arranging unit 26 is further adapted for giving an object of several objects, for which a similar degree of similarity is determined, priority depending on at least one feature, which has not been assigned by the initially assigning unit of the generating apparatus for generating a template. This feature, which determines the priority in the case of a similar degree of similarity, is preferentially the time, at which the, in this embodiment, medical image, which is preferentially the object, has been generated, in particular, has been acquired by a medical imaging device. In another embodiment, this feature could be the location of the part of the patient, which is shown by the respective medical image.

The arranging apparatus 28 further comprises a plausibility determination unit 27 for determining the plausibility of a feature of an object, wherein the similarity unit 25 and/or the arranging unit 26 are adapted for ignoring or considering with a reduced weight a feature, of which the plausibility is below a predefined threshold.

In the storage unit 18 several templates can be stored. If several templates are stored in the storage unit 18, a selecting unit 34 of the arranging apparatus 28 can be used for selecting one template of the multiple templates stored in the storage unit 18. For selecting a template, several templates are transferred from the storage unit 18 to the similarity unit 25. Furthermore, the objects, which have to be arranged on the places, are transferred from the providing unit 2 to the similarity unit 25. The similarity unit 25 determines for each combination of the places of the several templates with the objects provided by the providing unit 2 a degree of similarity. These determined degrees of similarity of the several combinations are transferred to the selecting unit 34, which determines for each template a degree of similarity resulting from the determined degrees of similarity of the combinations, which correspond to the respective template. In particular, the degrees of similarity of the combinations, which correspond to a template, are summed up for determining a degree of similarity of the respective template. The selecting unit 34 is preferentially further adapted for selecting the template having the highest degree of similarity. The selection, in particular, the selected template or information indicating the selected template, is transferred to the arranging unit 26 for arranging the objects at the places in accordance with the selected template. In another embodiment, the selection unit 34 can be omitted and, for example, a user can select a desired template via the input unit 29.

Figure 5:
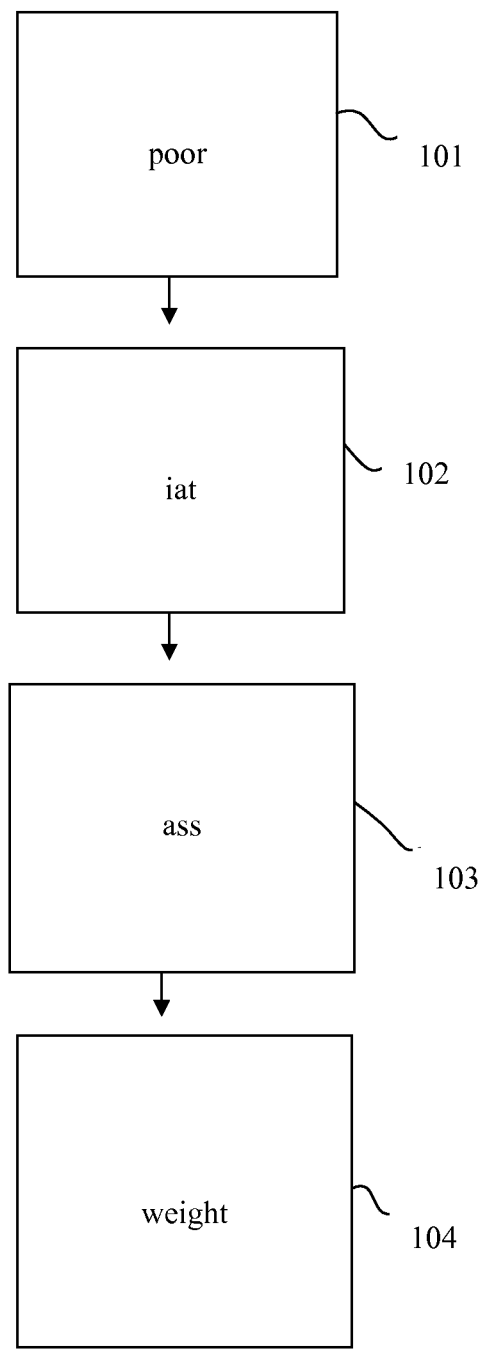
FIG. 5 shows exemplarily a flow chart for illustrating an embodiment of a method for generating a template for arranging at least one object at least one place.

In the following a preferred embodiment of a method for generating a template for arranging at least one object at least one place will be exemplarily described with reference to a flow chart shown in FIG. 5.

In step 101, at least one initial object, in this embodiment, several images, for generating a template are provided by the providing unit 2. These images preferentially belong to the same medical case, in particular, to the same examination of a patient.

The provided at least one initial object is arranged at at least one place in step 102. In this embodiment, the medical images 13, 14, 15, 16 are arranged at the places 9, 10, 11, 12 on the screen 31 of the monitor 30.

In step 103 a template 33 is generated by assigning features, which characterize the objects 13, 14, 15, 16 arranged at the places 9, 10, 11, 12, to the respective places.

In step 104, a weight, which is, in this embodiment, predefined, is assigned to each feature of the template 33, in particular, to each kind of features of the template 33.

In other embodiments, step 104 can be omitted.

Figure 4:
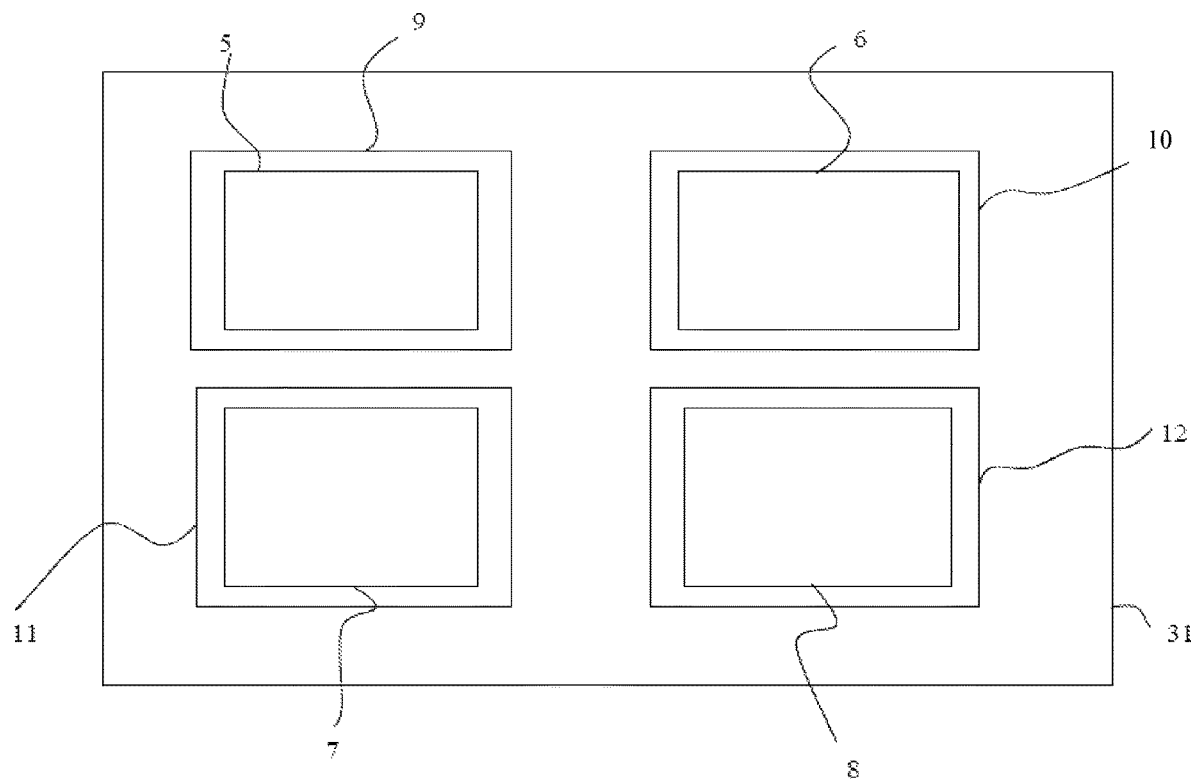
FIG. 4 shows schematically and exemplarily the screen, on which the places are distributed, wherein objects are arranged at the places in accordance with the template.
Figure 6:
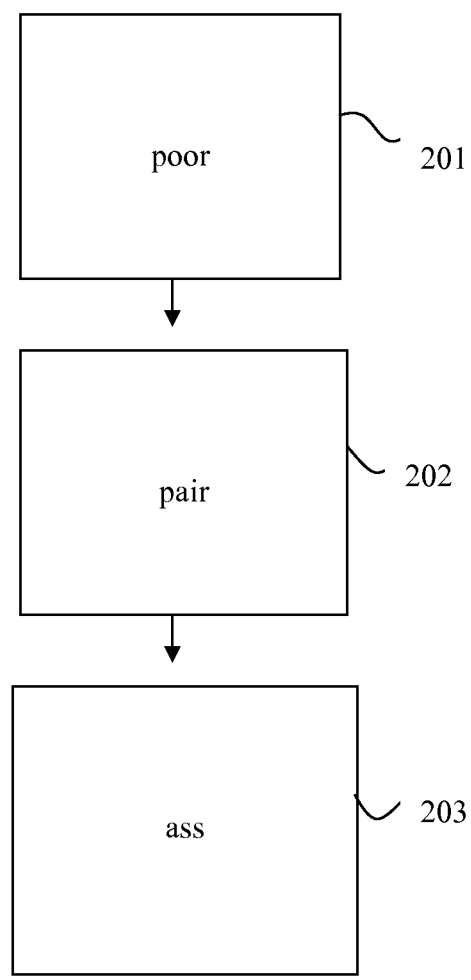
FIG. 6 shows exemplarily a flow chart for illustrating an embodiment of a method for arranging at least one object at at least one place using the template.

In the following an embodiment of a method for arranging at least one object at at least one place using a template will be exemplarily described with reference to a flow chart shown in FIG. 6. The method will be described with reference to FIG. 4 that shows a screen 31 with objects 5, 6, 7, and 8 arranged thereon.

In step 201 a template, in particular, the template 33 and objects, in particular, medical images, in particular, belonging to the same medical case, are provided to the similarity unit 25.

In step 202 the similarity unit 25 determines a degree of similarity for each combination of the provided objects 5, 6, 7, 8 and the places 9, 10, 11, 12 with respect to the features, which characterize the object, and the features assigned to the respective place in the template.

In step 203, the arranging unit 26 arranges the objects 5, 6, 7, 8 at the places 9, 10, 11, 12 depending on the determined similarities, in particular, firstly the object of the combination having the highest degree of similarity is arranged on the corresponding place, secondly the object of the combination having the second highest degree of similarity is arranged on the corresponding place, without considering combinations comprising an object, which has been arranged already, and a place, at which an object has been arranged already, and so forth.

The template can be implicitly and intuitively defined, in particular, by using a drag-and-drop operation, by which a user can arrange arbitrary objects, in particular, medical images at places on the screen. This arrangement of objects is stored as a template such that it can be restored at any time not only for the objects, i.e. the initial objects, which have been used for generating the template, but for any other future or existing group of objects, that are somehow similar to the initial objects.

Preferentially, a group of initial objects is used for generating a template. Further objects should be displayed in accordance with the template, wherein also these objects form preferentially a group. A group of initial objects or objects is preferentially a group of images, which belong to the same medical case, for example, to the same examination of the same patient.

The generation of the template by arranging initial objects at the places, in particular, by using a drag-and-drop operation, can be referred to as implicit in contrast to more explicit rule-based methods for generating templates.

The group or set of features, which are assigned to the places and which are used for determining a degree of similarity, is preferentially a subgroup of all features, which characterize the initial objects for generating the template and the further objects. This subgroup can be called fingerprint, i.e. a fingerprint comprises a set of features derived from the objects, in particular, derived from images, in particular, from the associated information that is stored with the images, in particular, in the DICOM standard.

The image, in particular, the medical image, comprises preferentially only one or several two-dimensional images forming a three-dimensional image. An object or initial object being a three-dimensional image can have three spatial dimensions or two spatial dimensions and one temporal dimension. Furthermore, an object or an initial object can also be a four-dimensional image having three spatial dimensions and one temporal dimension.

The arranging apparatus 28, in particular, the arranging unit 26 comprises rules how to arrange objects in a situation where, on the one hand, multiple objects from a given object group, for example from a given case or examination, are estimated to be equally similar or, on the other hand, no object from a given object group is estimated to be sufficiently similar to a given place with respect to the features of the respective object and the features assigned to the given place.

Although in the above described embodiments the features are substantially features of the DICOM standard, in other embodiments, other features of the objects can be used. For example, if the objects are images, features extracted from the images itself can be used for the generation of the template and the arrangement of further images in accordance with the generated template.

In the above described embodiments, a 2×2 viewer grid is described. But, in other embodiments, another arrangement of places, in particular, another viewer grid, for example, a 3×3 viewer grid can be used for displaying, for example, four or nine images, in particular image series, on a single or on several screens. In a specific editor, a user could also refine and extend the available viewer grids, i.e. a user could modify the arrangement of places on the screen.

Although in the above described template 33 weights $w_1 \ldots w_{11}$ are included, in other embodiments the template could only comprise the features needed for calculating the degree of similarity.

The providing unit 2 and the storage unit 18 can be regarded as belonging to the generation apparatus and the arranging apparatus or to none of them.

Other variations to the disclosed embodiments can be understood and effected by those skilled in the art and practicing the claimed invention, from a study of the drawings, the disclosure, and the appended claims.

In the claims the word "comprising" does not exclude other elements or steps and the indefinite article "a" or "an" does not exclude a plurality.

A single processor or other unit may fulfill the functions of several items recited in the claims. The mere fact that certain measures are recited in mutually different dependent claims does not indicate that a combination of these measures can not be used to advantage.

Determinations, calculations and assignments and the like, which are performed by one or several units or devices, can be performed by any other number of units or devices. For example, the functions of the units of the generating apparatus and the functions of the units of the arranging apparatus can be performed by a single unit or by any other number of units.

The calculations, determinations and assignments and the like and/or a control of the apparatuses in accordance with the methods in accordance with the invention can be implemented as program code means of a computer program and/or as dedicated hardware.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope of the invention.

The invention claimed is:

1. An apparatus including at least a processor for generating a template for arranging at least one object in at least one place on at least one screen of a monitor, wherein the at least one object is characterized by at least one feature, the template associating one or more features with one or more places on the at least one screen, wherein the apparatus comprises:
    a providing unit configured to provide a plurality of initial objects comprising medical images;
    an initially arranging unit configured to arrange the plurality of initial objects responsive to user input, each of the plurality of initial objects arranged at at least one respective place on the at least one screen, wherein the initially arranging unit is configured to allow the user to arrange each of the plurality of initial objects at respective places on the at least one screen by user placement of each of the plurality of initial objects at a respective place on the at least one screen;
    an assigning unit configured to automatically generate the template by, for each initial object of the plurality of arranged initial objects, automatically assigning, to a place in the template corresponding to the respective place on the at least one screen of the arranged initial object, multiple features derived from stored information associated with the arranged initial object, each one of the multiple features being a numerical or alpha-numerical data value and each one of the multiple features assigned a weight,
    wherein the template is generated such that, based on the template, a second object comprising a medical image to be arranged is automatically arrangeable at one of the respective places on the at least one screen by:
        a) determining a degree of similarity of multiple features of the second object to the multiple features and associated weights of each of the multiple features assigned to at least one place in the template corresponding to one respective place of one of the arranged initial objects on the at least one screen, and
        b) automatically arranging the second object at the one of the respective places on the at least one screen depending on the determined degree of similarity; and
    a storing unit for storing the generated template.

2. The apparatus as defined in claim 1, further comprising a modifying unit configured to modify the template by modifying an arrangement of one or more of the plurality of initial objects at their respective places.

3. An apparatus, including at least a processor, for arranging a second object in at least one place on at least one screen of a monitor using an automatically generated template, wherein the second object is characterized by at least one feature having a numerical or alpha-numerical data value, wherein the apparatus is provided with a template generated by an apparatus for automatically generating a template, and wherein the apparatus for automatically generating a template comprises:
    a providing unit configured to provide a plurality of initial objects comprising medical images, each initial object characterized by a plurality of features from information associated with and stored with the initial object;
    an initially arranging unit configured to receive from a user an arrangement of the plurality of initial objects in respective places on the at least one screen by user placement of each of the plurality of initial objects at a respective place on the at least one screen;
    an assigning unit configured to automatically generate the template by, for each initial object of the plurality of initial objects, automatically assigning, to a place in the template corresponding to the respective place of the initial object arranged on the at least one screen, multiple features derived from information associated with and stored with the initial object, each of the multiple features being a numerical or alpha-numerical data value and each of the multiple features assigned a weight;
    a storing unit for storing the generated template; and
    wherein the apparatus for arranging the second object comprising a medical image in the at least one place on at least one screen of the monitor using the automatically generated template comprises:
        a similarity unit for determining a degree of similarity of multiple features of the second object to the multiple features and associated weights assigned to at least one of the places in the template corresponding to one respective place on the at least one screen; and
        an arranging unit for arranging the second object at one of the respective places on the at least one screen depending on the determined degree of similarity.

4. The apparatus as defined in claim 3, wherein multiple objects to be arranged and multiple places in the template are present, wherein the similarity unit is operable to determine a degree of similarity for each combination of the multiple objects to be arranged with respect to the multiple places in the template, and wherein the arranging unit is operable to arrange the multiple objects to be arranged at places on the at least one screen that correspond to the multiple places in the template in accordance with the determined degrees of similarity of the combinations.

5. The apparatus as defined 3, wherein the arranging unit is operable to arrange the second object at one of the respective places on the at least one screen only if the determined similarity exceeds a predetermined threshold.

6. The apparatus as defined in claim 3, wherein, when the second object is not arranged on one of the respective places, the object is assigned to a remaining list.

7. The apparatus as defined in claim 3, wherein multiple objects to be arranged are present and wherein the arranging unit of the apparatus is operable to arrange one or more of the multiple objects for which a similarity degree of similarity is determined in dependence on features of these multiple objects, wherein the one or more of the multiple objects have not been already assigned by the assigning unit of the apparatus for generating the template.

8. The apparatus as defined in claim 3, further comprising a plausibility determination unit for determining the plausibility of a feature of the second object to be arranged by the arranging unit of the apparatus, wherein the similarity unit and/or the arranging unit are operable to ignore or consider with a reduced weight a feature with a determined plausibility below a predefined threshold.

9. The apparatus as defined in claim 3, wherein the apparatus for automatically generating a template is operable to provide multiple templates, wherein the apparatus for arranging further comprises a selecting unit for selecting a template of the multiple templates by determining for each template a degree of similarity to one or more objects to be arranged, and by selecting a template of the multiple templates having the degree of similarity above a threshold and/or having a maximum degree of similarity to the object.

10. A method for automatically generating a template for arranging at least one object to be arranged in at least one place on at least one screen of a monitor, wherein the at least one object to be arranged is characterized by at least one feature, the template associating one or more features with one or more places on the at least one screen, comprising:
  providing a plurality of initial objects comprising medical images;
  under control of a processor of a computer system, providing a graphical user interface configured to allow a user to arrange the each of the initial objects at the respective places on the at least one screen by placing each of the initial objects on the at least one screen;
  under control of the processor of the computer system, automatically generating the template by, for each initial object of the plurality of initial objects, automatically assigning, to a place in the template that corresponds to the respective place on the at least one screen, multiple features derived from information associated with and stored with the initial object that is arranged at the respective place, each of the multiple features of each initial object being a numerical or alpha-numerical data value and each of the multiple features assigned a weight,
  wherein the template is automatically generated such that, based on the template, a second object comprising a medical image and that is an object to be arranged is arrangeable at one of the respective places on the at least one screen by:
    a) automatically determining a degree of similarity of at least one feature of the second object to the multiple features and associated weights assigned to at least one of the places in the template corresponding to one respective place of one of the arranged initial objects on the at least one screen; and
    b) automatically arranging the second object at one of the respective places on the at least one screen depending on the determined degree of similarity; and
  under control of the processor of the computer system, storing the generated template in a storing unit.

11. A method for automatically arranging a second object in at least one place on at least one screen of a monitor using a template, wherein the object is characterized by at least one feature having a numerical or alpha-numerical data value, wherein the template is automatically generated by:
  providing a plurality of initial objects, each initial object comprising a medical image and characterized by a plurality of features from information associated with and stored with the initial object;
  arranging the plurality of initial objects in the respective places on the at least one screen in response to user placement and arrangement of the initial objects in the respective places;
  under control of a computer processor of a computer system automatically generating the template by, for each initial object of the plurality of initial objects, automatically assigning, to a place in the template corresponding to the respective place of the initial object arranged on the at least one screen, multiple features derived from information associated with and stored with the initial object, each of the multiple features being a numerical or alpha-numerical data value and each of the multiple features assigned a weight;
  storing the generated template in a storing unit; and
  wherein the method for arranging the second object comprising a medial image in the place on the at least one screen of the monitor using the automatically generated template comprises:
    under control of a computer processor of a computer system,
      automatically determining a degree of similarity of multiple features of the second object to the multiple features and associated weights assigned to at least one of the places in the template corresponding to one respective place of one of the arranged initial objects on the at least one screen; and
      automatically arranging the second object at one of the respective places on the at least one screen depending on the determined degree of similarity.

12. A non-transitory storage medium containing a computer program for automatically generating a template for arranging a second object in at least one place on at least one screen of a monitor, wherein the computer program comprises program code that is operable to cause a computer processor of a computer system to carry out instructions, comprising:
  providing a plurality of initial objects comprising medical images;
  providing a graphical user interface configured to allow a user to arrange the initial objects at respective places on the at least one screen by placing each of the initial objects on the at least one screen;
  automatically generating the template by automatically assigning, to each place in the template that corresponds to each of the respective places on the at least one screen, multiple features derived from information associated with and stored with the initial object that has been arranged at the respective place, each of the multiple features being a numerical or alpha-numerical data value and each of the multiple features assigned a weight,
  wherein the template is automatically generated such that, based on the template, a second object comprising a medical image and that is an object to be arranged is arrangeable at one of the respective places on the at least one screen by:
  a) automatically determining a degree of similarity of at least one feature of the second object to the multiple features and associated weights assigned to at least one of the places in the template corresponding to one respective place on the at least one screen; and
  b) automatically arranging the second object at the one of the respective places on the at least one screen depending on the determined degree of similarity; and
storing the generated template in a storing unit.

13. A non-transitory storage medium containing a computer program for automatically arranging a second object in at least one place on at least one screen of a monitor using a template wherein the computer program comprises program code operable to cause a computer processor of a computer system to carry out instructions, comprising:
  providing a plurality of initial objects, each initial object comprising a medical image and characterized by a plurality of features from information associated with and stored with the initial object;
  arranging the plurality of initial objects at respective places on the at least one screen in response to user placement and arrangement of the initial objects in the respective places;
  automatically generating the template by automatically assigning, to each place in the template corresponding to each of the respective places on the at least one screen multiple features derived from information associated with and stored with the initial object that has been arranged at the respective place, each of the multiple features being a numerical or alpha-numerical data value and each of the multiple features assigned a weight;
  storing the generated template in a storing unit;
  automatically determining a degree of similarity of multiple features of the second object to the multiple features and associated weights assigned to at least one of the places in the template corresponding to the one respective place on the at least one screen; and
  automatically arranging the second object at the one of the respective places on the at least one screen depending on the determined degree of similarity.

14. An apparatus including at least a processor for automatically generating a template for arranging at least one object in at least one place on at least one screen of a monitor, wherein the at least one object is characterized by at least one feature having a numerical or alpha-numerical data value, wherein the apparatus comprises:
  a providing unit configured to provide a plurality of initial objects comprising medical images;
  an initially arranging unit configured to arrange the plurality of initial objects at respective places on the at least one screen in response to user placement of the initial objects at the respective places on the at least one screen;
  an assigning unit configured to automatically generate the template by, for each initial object of the plurality of arranged initial objects, automatically assigning, to a place in the template corresponding to the respective place of the arranged initial object on the at least one screen, at multiple features derived from stored information associated with the arranged initial object, each one of the multiple features being a numerical or alpha-numerical data value and each one of the multiple features assigned a weight,
  wherein the template is generated such that, based on the template, a second object comprising a medical image to be arranged is automatically arrangeable at one of the respective places on the at least one screen by:
    a) determining a degree of similarity of multiple features of the second object to the multiple features and associated weights assigned to at least one of the places in the template corresponding to one respective place on the at least one screen, and
    b) automatically arranging the second object at one of the respective places on the at least one screen depending on the determined degree of similarity; and
  a modifying unit configured to modify the automatically generated template responsive to user input by allowing the user to modify an arrangement of at least one of the initial objects at its respective place by user placement of the at least one of the initial objects at a different respective place on the at least one screen.

15. A method for automatically generating a template for automatically arranging at least one object in at least one place on at least one screen of a monitor, wherein the at least one object is characterized by at least one feature having a numerical or alpha-numerical data value, comprising:
  providing a plurality of initial objects comprising medical images;
  arranging the plurality of initial objects at respective places on the at least one screen in response to user placement of the initial objects at the respective places on the at least one screen;
  under control of a computer processor of a computer system, automatically generating the template by, for each initial object of the plurality of arranged initial objects, automatically assigning to a place in the template, corresponding to the respective place of the arranged initial object on the at least one screen, multiple features derived from stored information associated with the arranged initial object, each one of the multiple features being a numerical or alpha-numerical data value and each one of the multiple features assigned a weight,
  wherein the template is generated such that, based on the template, a second object comprising a medical image to be arranged is automatically arrangeable at one of the respective places on the at least one screen by:
    a) determining a degree of similarity of multiple features of the second object to multiple features and associated weights assigned to at least one of the places in the template corresponding to one respective place on the at least one screen, and
    b) automatically arranging the second object at one of the respective places on the at least one screen depending on the determined degree of similarity; and
  under control of a computer processor of a computer system, automatically modifying the template in response to user input of a modified arrangement of one of the initial objects from its respective place to another place, wherein a graphical user interface is provided and configured to allow a user to modify the arrangement by placement of the one of the initial objects to the another place.

16. A non-transitory storage medium containing a computer program for automatically generating a template for arranging an object in at least one place on at least one screen of a monitor, wherein the computer program comprises program code that is operable to cause a computer processor of a computer system to carry out instructions, comprising:

provide a plurality of initial objects, each initial object comprising a medical image and characterized by a plurality of features from information associated with and stored with the initial object;

arranging the plurality of initial objects at respective places on the at least one screen in response to user placement of the initial objects in the respective places;

automatically generating the template by, for each initial object of the plurality of arranged initial objects, automatically assigning, to a place in the template corresponding to the respective place on the at least one screen of the arranged initial object, multiple features derived from the information associated with and stored with the arranged initial object, each of the multiple features being a numerical or alpha-numerical data value and each of the multiple features assigned a weight, wherein the template is generated such that, based on the template, a second object comprising a medical image to be arranged is automatically arrangeable at one of the respective places of one of the arranged initial objects on the at least one screen by:

a) determining a degree of similarity of multiple features of the second object to multiple features and associated weights assigned to at least one of the places in the template corresponding to one respective place on the at least one screen, and b) arranging the second object at one of the respective places on the at least one screen depending on the determined degree of similarity; and automatically modifying the template in response to user input of a modified arrangement of at least one of the initial objects from its respective place to another place, wherein a graphical user interface is provided and configured to allow a user to modify the arrangement by placement of the one of the initial objects to the another place.

17. The apparatus as defined in claim 2 wherein the arrangement is modified by substituting at least one different object for one of the initial objects at a respective place on the screen, adding another initial object to another respective place on the screen, and/or deleting one of the plurality of initial objects from its respective place on the screen, thereby causing the multiple features and associated weights assigned to one or more places in the template to be modified.

18. The apparatus as defined in claim 14 wherein the arrangement is modified by substituting at least one different object for one of the initial objects at a respective place on the screen, adding another initial object to another respective place on the screen, and/or deleting one of the plurality of initial objects from its respective place on the screen, thereby causing one or more the multiple features and associated weights assigned to one or more places in the template to be modified.

* * * * *

UNITED STATES PATENT AND TRADEMARK OFFICE
CERTIFICATE OF CORRECTION

Page 1 of 1

PATENT NO. : 10,916,043 B2
APPLICATION NO. : 11/945106
DATED : February 9, 2021
INVENTOR(S) : Horst Hahn et al.

It is certified that error appears in the above-identified patent and that said Letters Patent is hereby corrected as shown below:

In the Claims

In Column 14, Line 64 (Claim 5), before "3" insert --in claim--.

In Column 20, Line 27 (Claim 18), after "more" insert --of--.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*